US 6,562,058 B2

(12) United States Patent
Seguin et al.

(10) Patent No.: US 6,562,058 B2
(45) Date of Patent: May 13, 2003

(54) INTRAVASCULAR FILTER SYSTEM

(75) Inventors: Jacques Seguin, 18 rue Montalivet, 75009 Paris (FR); Jean-Claude Laborde, Vieille Toulouse (FR); Georg Bortlein, Courbevoie (FR)

(73) Assignee: Jacques Seguin (FR)

( * ) Notice: Subject to any disclaimer, the term of this patent is extended or adjusted under 35 U.S.C. 154(b) by 0 days.

(21) Appl. No.: 09/796,693

(22) Filed: Mar. 2, 2001

(65) Prior Publication Data
US 2002/0123766 A1 Sep. 5, 2002

(51) Int. Cl.[7] .............................................. A61M 29/00
(52) U.S. Cl. ....................................................... 606/200
(58) Field of Search .................................. 606/200, 159, 606/158, 194, 198, 191, 195

(56) References Cited

U.S. PATENT DOCUMENTS

| 3,996,938 | A |   | 12/1976 | Clark, III |
|---|---|---|---|---|
| 4,650,466 | A |   | 3/1987 | Luther |
| 4,926,858 | A |   | 5/1990 | Gifford, III |
| 4,991,602 | A |   | 2/1991 | Amplatz et al. |
| 5,053,008 | A |   | 10/1991 | Bajaj |
| 5,067,489 | A |   | 11/1991 | Lind |
| 5,108,419 | A |   | 4/1992 | Reger et al. |
| 5,160,342 | A |   | 11/1992 | Reger et al. |
| 5,329,942 | A |   | 7/1994 | Gunther et al. |
| 5,354,310 | A | * | 10/1994 | Garnic et al. |
| 5,490,859 | A |   | 2/1996 | Mische et al. |
| 5,669,933 | A | * | 9/1997 | Simon et al. |
| 5,695,519 | A |   | 12/1997 | Summers et al. |
| 5,769,816 | A |   | 6/1998 | Barbut et al. |
| 5,795,322 | A |   | 8/1998 | Boudewijn |
| 5,810,874 | A |   | 9/1998 | Lefebvre |
| 5,814,064 | A |   | 9/1998 | Daniel et al. |
| 5,836,868 | A |   | 11/1998 | Ressemann et al. |
| 5,897,567 | A |   | 4/1999 | Ressemann et al. |
| 5,910,154 | A |   | 6/1999 | Tsugita et al. |
| 5,911,734 | A |   | 6/1999 | Tsugita et al. |
| 5,935,139 | A |   | 8/1999 | Bates |
| 5,941,869 | A |   | 8/1999 | Patterson et al. |
| 5,941,896 | A |   | 8/1999 | Kerr |
| 5,951,585 | A |   | 9/1999 | Cathcart et al. |
| 5,954,745 | A |   | 9/1999 | Gertler et al. |
| 5,957,949 | A |   | 9/1999 | Leonhardt et al. |
| 5,976,172 | A |   | 11/1999 | Homsma et al. |
| 5,980,555 | A |   | 11/1999 | Barbut et al. |
| 5,989,281 | A |   | 11/1999 | Barbut et al. |
| 6,001,118 | A |   | 12/1999 | Daniel et al. |
| 6,013,093 | A |   | 1/2000 | Nott et al. |

(List continued on next page.)

FOREIGN PATENT DOCUMENTS

| DE | 198 11 364 A1 | 9/1999 |
|---|---|---|
| WO | WO 96/01591 | 1/1996 |
| WO | WO 98/33443 | 8/1998 |
| WO | WO 99/23976 | 5/1999 |
| WO | WO 99/44510 | 9/1999 |
| WO | WO 00/16705 | 3/2000 |
| WO | WO 00/49970 | 8/2000 |

Primary Examiner—Ismael Izaguirre
(74) Attorney, Agent, or Firm—Oliff & Berridge, PLC

(57) ABSTRACT

A removable intravascular filter system traps emboli and other solid materials in connection with intravascular medical procedures such as the placement of a stent or a catheter balloon. The system involves a hollow guidewire and an actuating wire movable within the guidewire to actuate the filter membrane. Embodiments of the filter system include biased closed and biased open filter configurations, and are easily routed through a patient's artery and deployed. Optionally, the actuating wire can be removed and a substitute wire can be inserted into the hollow guidewire. Control mechanisms can help the operator limit movement of the actuating wire during deployment and/or collapse of the filter membrane. Preferred filter membranes are configured to maximize both blood flow and emboli capture.

61 Claims, 10 Drawing Sheets

U.S. PATENT DOCUMENTS

| | | |
|---|---|---|
| 6,027,520 A | 2/2000 | Tsugita et al. |
| 6,042,598 A | 3/2000 | Tsugita et al. |
| 6,053,932 A | 4/2000 | Daniel et al. |
| 6,059,814 A | 5/2000 | Ladd |
| 6,066,149 A | 5/2000 | Samson et al. |
| 6,068,645 A | 5/2000 | Tu |
| 6,074,357 A | 6/2000 | Kaganov et al. |
| 6,086,605 A | 7/2000 | Barbut et al. |
| 6,096,053 A | 8/2000 | Bates |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita et al. |
| 6,146,396 A | 11/2000 | Konya et al. |
| 6,152,946 A | 11/2000 | Broome et al. |
| 6,152,947 A | 11/2000 | Ambrisco et al. |

* cited by examiner

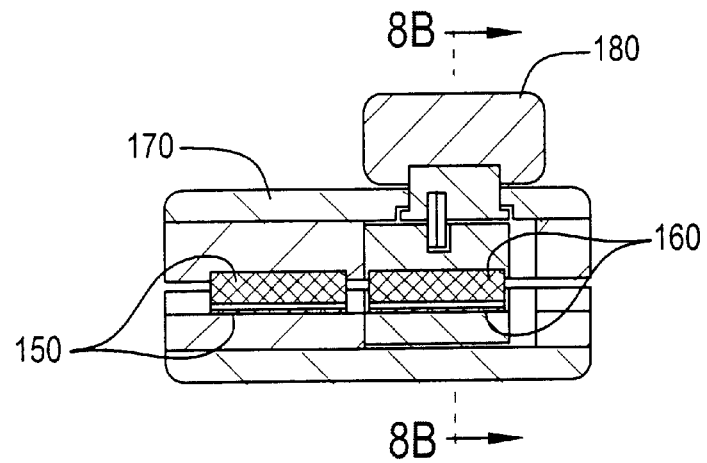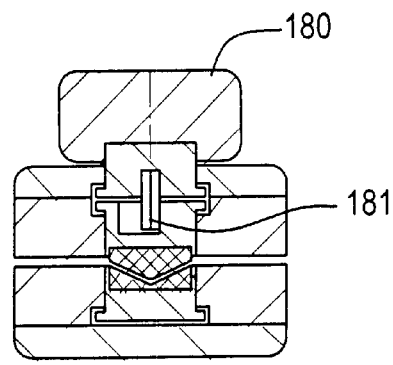
Fig. 8A　　　　　　　　Fig. 8B
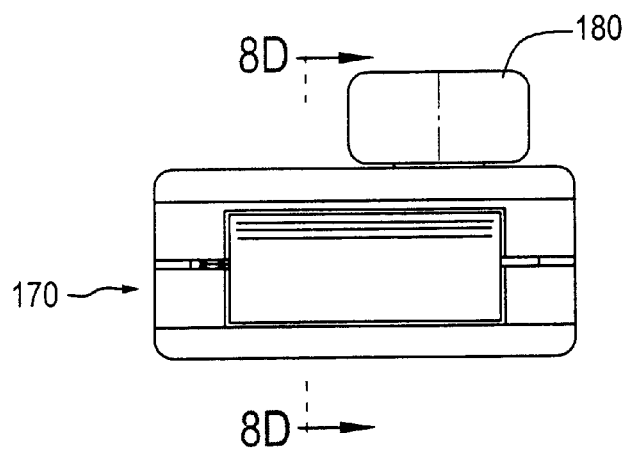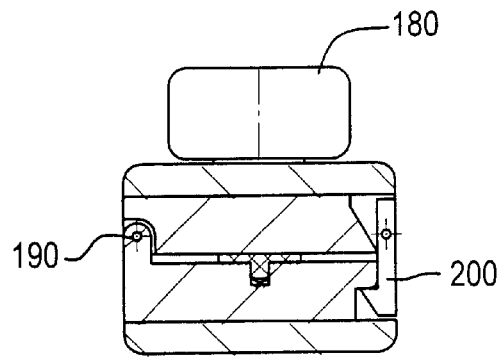
Fig. 8C　　　　　　　　Fig. 8D

INTRAVASCULAR FILTER SYSTEM

BACKGROUND OF THE INVENTION

1. Field of Invention

The invention relates to a removable intravascular filter system used in connection with intravascular medical procedures, the purpose of which is to prevent solid material from being released into the vascular system.

2. Description of Related Art

U.S. Pat. No. 5,941,896 reports that advances in medicine and technology are leading to the development of minimally invasive surgical techniques for treatment of various medical conditions. For example, stenosis formed in a blood vessel may be treated endovascularly using techniques such as balloon angioplasty, stent placement, or thrombolysis. However, the use of such endovascular techniques has been limited due to embolization of debris from the treated portion of the vessel to a downstream portion resulting in complications. For example, treatment of a stenosis in a carotid artery can result in ischemic complications and possible embolic stroke.

International Publication WO 99/44510 discloses a guidewire filter which has an elongate hollow tube with a proximal end, a distal end, an inside and an outside surface, and a lumen formed throughout. The hollow tube has a plurality of longitudinal slots forming a plurality of longitudinal rib portions near the distal region of the hollow tube. An actuating wire with a proximal end and a distal end is provided and is "permanently attached" to the distal end of the guidewire filter. Filter material is positioned within the lumen in the hollow tube. An activation handle on the proximal end of the device is provided for pulling the actuating wire relative to the hollow tube. An object of the invention is to provide for a guidewire filter in which the filter is deployed by "pulling" rather than by pushing on an actuating wire allowing use of a thinner wire; although, optionally, the hollow tube can be pushed relative to the actuating wire to deploy the filter. The actuating wire is taught to be only as thick as possible to carry the force required to activate the filter assembly yet to provide as much room as possible for the filter material to fit inside the outer hollow tube. A disadvantage of this technology is that the actuating wire is permanently attached to the guidewire filter and must remain in place during the entire procedure, subjecting the artery to a possibly too rigid two layer guidewire.

International Publication WO 00/16705 discloses a removable vascular filter system for blocking micro and macro emboli while allowing continual blood circulation. The device comprises a guidewire and a filter assembly which is attached to the guidewire at the guidewire's distal end. A movable core wire is attached to the filter assembly to actuate it. Attachment of the filter membrane to the guidewire is taught to allow expansion of the filter membrane with a firm fit inside the artery and to allow for collapse of the membrane tightly through the guidewire. The guidewire is used for the entire procedure from crossing a lesion to deploying a stent. Embodiments of the invention include a filter membrane consisting of a thin membrane attached to the guidewire and supported by metal spines. Another embodiment comprises a filter membrane which rests upon or is attached to a basket-like structure, which is attached to a guidewire at one end. Yet another embodiment uses a retractable sheath at the distal end of the guidewire which covers the filter membrane in the collapsed state. The sheath distal portion is affixed to the guidewire tip, which is affixed to the distal end of the movable core and is taught to prevent the filter membrane from becoming entangled in an artery or guide catheter.

A disadvantage of an external sheath design is that it increases the diameter of the filter system in a patient's arteries, which is especially important with the sheath going over an arterial lesion before and after a medical procedure. In the device of WO 00/16705, the filter membrane must be affixed at least at its distal portion to the core wire and/or basket wire distal ends.

International Publication WO 99/23976 discloses an embolic protection device comprising a collapsible filter element which is slidably mounted on a guidewire for axial movement along the guidewire. The device is equipped with stoppers to limit axial movement along the guidewire. The filter element collapses into the outer end of a catheter for deployment and retrieval through the vascular system of a patient. The filter element has a collapsible filter body with a proximal inlet end and a distal outlet end. After use, the catheter is movable along the guidewire to engage the proximal end of the filter element and to close the inlet openings before sliding over the filter element from the proximal end to the distal end to progressively collapse the filter body on the guidewire for retrieval. The catheter acts as a sheath to protect the vessel walls during deployment and retrieval of the filter element. The filter element is attached to a shaft that can run over the primary guidewire and that is attached on one portion of the filter element. Moreover, filter membrane designs are taught which reduce the longitudinal length of creases which may occur should the filter be oversized, acting as crease breakers. Membrane designs are also taught which include a series of channels or pathways.

This design also relies on the use of sheaths which add to the rigidity of the device in the patient's arteries and add to the radial dimension and size of the device.

U.S. Pat. No. 6,142,987 to Tsugita et al. discloses a guided filter system for temporary placement of a filter in an artery or vein. The system includes a guidewire slideable through a wire guide included at a distal region of a support wire. The support wire has an expandable filter, which is operable between a collapsed and an enlarged condition and is attached to the support wire. A variety of endovascular devices, including angioplasty, artherectomy, and stent deployment catheters, are insertable over the guidewire and/or the support wire. Various embodiments of the invention include an expandable filter which is mounted at the distal region of the support wire, as well as capture sheaths. Methods of using the guided filter system to direct and exchange endovascular devices to a region of interest, and to entrap and remove embolic material from the vessel are also disclosed.

U.S. Pat. No. 5,941,986 to Kerr discloses a filter and method for trapping emboli during endovascular procedures. In one embodiment, the filter is formed from a bent, flexible guidewire shaped to define a frame and a porous filtering material attached to portions thereof. In a collapsed state, the filter can readily pass through the lumen of a catheter and into the bloodstream of a patient. Upon completion of an endovascular procedure, the filter is collapsed and retracted into the catheter. In alternative embodiments of the invention, porous filtering material is mounted to external portions of a catheter, and a control guidewire is attached to the filtering material to selectively control the filter between the open and closed states.

International Publication WO 96/01591, by Mazzochi et al. discloses a vascular trap comprising an umbrella-shaped basket carried adjacent a distal end of a guidewire. The guidewire includes a tapered distal section with a spirally wound coil basket extending along a distal length of the wire. The basket is positioned generally distally of the coil and is preferably attached to the guidewire proximal of the proximal end of the tapered section. The basket may be attached by means of tethers which are attached to the guidewire by means of metal straps. The basket may be closed by pulling the guidewire into a sheathing catheter.

U.S. Pat. No. 6,027,520 to Tsugita et al. discloses an apparatus and method for preventing detachment of mobile aortic plaque within the ascending aorta, the aortic arch, or the carotid arteries, and to an apparatus and method for providing a stent and a filter in a percutaneous catheter for treating occlusions within the carotid arteries. The embodiments of this invention have a plurality of struts which are attached at a distal end of the guidewire and extend distally. The struts are connected to each other at each end and have an intermediate region which is biased to expand radially. The filter mesh is attached between the intermediate region and the distal end of the struts. In other embodiments the struts are attached to the distal end of the sheath. The struts extend distally from the sheath and attach to the distal end of the guidewire. Embodiments also include a filter mesh attached to struts between an intermediate region and distal end of the guidewire.

SUMMARY OF THE INVENTION

Embodiments of the invention provide a removable filter system with a simple actuating mechanism of few parts.

Embodiments of the invention provide a removable filter system which can be used in the blood vessels of a patient without the need for a sheath covering the filter.

Embodiments of the invention provide a filter system with the ability to select the rigidity of an actuating wire during positioning or deployment of the filter system and use of the guidewire.

Embodiments of the invention provide a removable filter system which can be deployed without the filter membrane being permanently fixed or attached to the actuating wire.

Embodiments of the invention provide a self-contained, removable filter system that has a slender diameter and presents a reduced risk of dislodging embolic material during positioning.

Embodiments of the invention provide a removable filter system that allows deployment of a filter assembly comprising a filter membrane which is biased in either the closed or the open position. An actuating wire is inserted through the proximal end of the filter assembly and engages the filter assembly to deploy or collapse the filter assembly.

Embodiments of the invention provide a filter system comprising a filter assembly which has a distal and a proximal end, a hollow guidewire which is connected to the proximal end of the filter assembly, and an actuating wire which is longitudinally movable through the lumen of the hollow guidewire but not affixed to the filter assembly. The actuating wire is engageable with the filter assembly at the filter assembly's distal end.

Embodiments of the invention provide an intravascular filter with distinctive shapes that reduce the clogging effect due to trapped emboli.

Embodiments of the invention provide a control device to prevent unwanted displacement of the actuating wire.

Embodiments of the invention provide a control mechanism for operating the actuating wire with a locking mechanism which allows a pre-defined movement of the actuating wire and prevents damage to the filter.

In embodiments where the filter system is biased open, the actuating wire may be advanced beyond the distal end of the hollow guidewire and engage the distal end of the filter assembly, collapsing the filter assembly to the closed position during movement through a vessel. The filter assembly deploys to the open position against a vessel wall upon retraction of the actuating wire. The actuating wire may optionally be entirely removed while the filter system is deployed or replaced with a wire of different rigidity. The filter system may be easily closed and readied for removal from a patient's circulation upon advancing of the actuating wire into the distal end of the filter system.

In embodiments where the filter assembly is biased closed, the distal end of the actuating wire may convert to any desirable three-dimensional configuration upon being advanced beyond the distal end of the hollow guidewire. The actuating wire then removably engages the filter assembly, deploying the filter assembly in the open position against the vessel wall. The actuating wire is easily retracted into the hollow guidewire so that the filter assembly closes for removal from a patient's circulation. Thus, the actuating wire may even be absent or replaced with an actuating wire of different rigidity during placement or removal of the hollow guidewire.

In embodiments, the present invention provides an intravascular filter having a cage which is supported by a plurality of ribs extending from the proximal end to the distal end of the cage. The ribs are constrained against radial movement to a vessel wall at the distal end of the cage. The ribs are radially movable into contact with the vessel wall, however, at the proximal end of the cage. A filter membrane is supported within the cage and includes a proximal portion that contains radial convexities extending radially outward between the ribs to contact the vessel wall when the filter is deployed.

In embodiments, the present invention provides an intravascular filter which contains a filter membrane which has a distal portion that includes radially extending concavities that extend inward between the ribs to assist in controlled folding of the intravascular filter for positioning or removal.

In embodiments, the present invention also provides an intravascular filter which has a filter membrane which when deployed has a proximal portion that is axially convex and a distal portion that is frustoconical or tubular and of a smaller diameter than the proximal portion.

In embodiments, the present invention provides for a device for controlling movement of an actuating wire through a lumen of a hollow guidewire, comprising a first, axially constrained gripper configured to grip a proximal portion a hollow guidewire, a second axially movable gripper configured to grip a portion of the actuating wire extending out of the proximal portion of the hollow guidewire, and a control member for moving the axially movable gripper over a predetermined axial distance.

In embodiments, the present invention provides for an intravascular filter system comprising a hollow guidewire which has an axially extending lumen, an actuating wire which extends through the lumen, a filter assembly that can be deployed or collapsed by the actuating wire, and a control mechanism. The control mechanism controls the extent of axial movement of the actuating wire through the lumen of the guidewire. The control mechanism has at least one projection on either an interior surface of the guidewire or an exterior surface of the actuating wire. In addition, the control mechanism has at least one indentation, such as a groove, for mating on either of the guidewire or the actuating wire.

In embodiments, the present invention provides a filter assembly, having a filter membrane made of a single sheet of material which can be folded or otherwise shaped mechanically to form the desired filter shape.

In embodiments, the present invention provides a filter assembly, having a filter membrane composed of polymeric material with laser cut holes or a single sheet of metal such as Nitinol® in which the membrane portion has laser cut holes.

In embodiments, the present invention provides a method of trapping and removing solid material from a vessel of a patient, using filter systems of the type described herein.

BRIEF DESCRIPTION OF THE DRAWINGS

FIG. 8A is a longitudinal cross-sectional view of a device for controlling movement of an actuating wire through the lumen of a hollow guidewire.

FIG. 8B is a transverse cross-section of the control device of FIG. 8A.

FIG. 8C is a side view of the lock side of the control device.

FIG. 8D is a transverse cross-section of the control device of FIG. 8C.

DETAILED DESCRIPTION OF PREFERRED EMBODIMENTS

Filter systems of the invention comprise a filter assembly which has a distal end and a proximal end and, which preferably also comprise a filter membrane. A hollow guidewire is connected to the proximal end of the filter assembly and forms a lumen throughout for slidable movement of an actuating wire. The connection may be achieved by integral formation or attachments such as threads, luer locks, or any other suitable attachment. The actuating wire may be inserted into or located within the hollow guidewire and is advanced beyond the hollow guidewire into the filter assembly. The actuating wire can then deploy or collapse the filter assembly, depending on whether the filter assembly is initially biased open or closed. The filter assembly can be tailored to different configurations to assume different shapes and sizes depending upon the nature of the medical procedure and the vessel involved. The filter assembly can be configured to be either biased closed or open. The filter system may be equipped to receive actuating wires of various dimensions, flexibilities, and configurations depending upon the medical procedure or vessel involved. According to embodiments of the present invention, a substitute wire may be inserted before insertion or after withdrawal of the actuating wire when a wire of a different flexibility or diameter is desired during movement or deployment of the filter assembly. The actuating wire is preferably not attached to the filter assembly. Embodiments of the invention also include preferred filter configurations and control mechanisms for the actuating wire.

According to the present invention, various filter systems are provided that can be used in connection with intravascular medical procedures such as the placing of a stent. U.S. Pat. No. 6,142,987, the disclosure of which is incorporated by reference, describes how other devices, such as an angioplasty catheter and balloon can be used in conjunction with a filter on a guidewire.

The actuating wire is longitudinally movable through the lumen of the hollow guidewire and preferably has the ability to engage and disengage the filter assembly without being affixed to the filter assembly. The actuating wire is used to deploy the filter assembly into the open position or to collapse the filter assembly into the closed position. In embodiments, the filter system has a biased open filter membrane which can be forced into a closed position by advancing an actuating wire through the lumen of the hollow guidewire and against the distal end of the filter assembly. In embodiments, the filter system has a biased closed filter membrane that can be forced into an open position by advancing an actuating wire through the lumen of the hollow guidewire and into the filter assembly with the actuating wire converting into a three-dimensional configuration against the filter assembly.

Figure 1A:
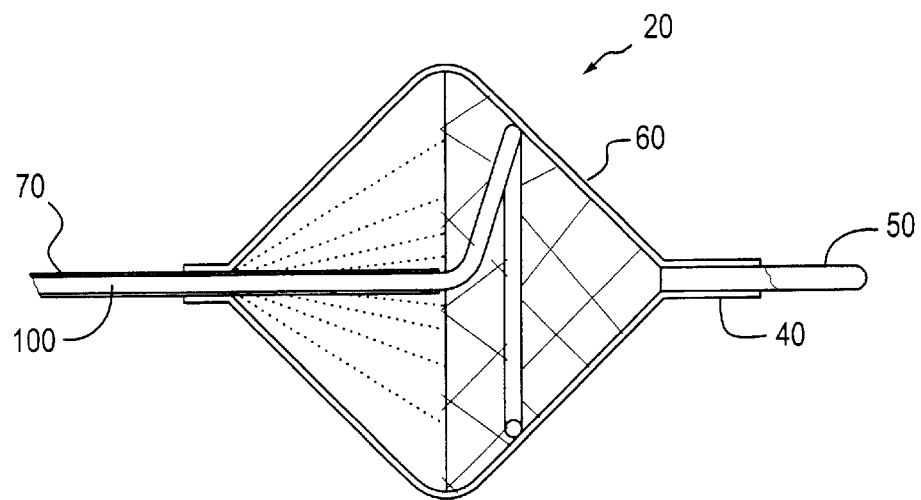
FIGS. 1A and 1B are plan views of a biased closed filter system of a first embodiment of the present invention.
Figure 1B:
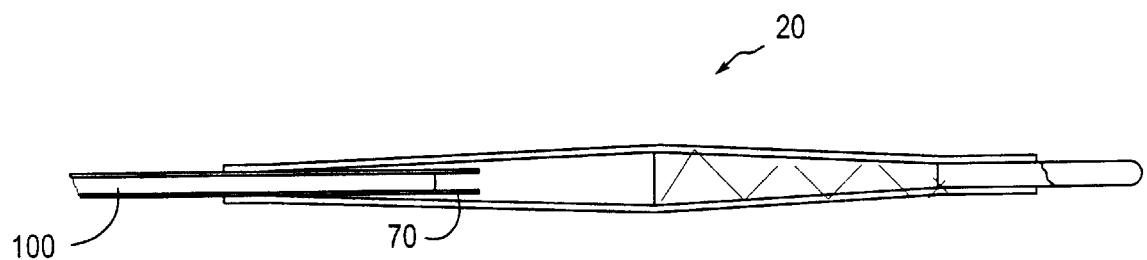

In a first embodiment shown in FIGS. 1A and 1B, a biased closed filter assembly 20 is advanced into the vessel of a patient until the treatment site is reached (FIG. 1B). The filter assembly 20 is then deployed in the open position (FIG. 1A) against a vessel wall by advancing the distal end of actuating wire 100 which, when unconstrained by the hollow guidewire 70, converts into the desired shape, and engages the filter assembly 20. Optionally, for example, the distal end of actuating wire 100 can form a lasso or spiral shape which engages the filter assembly 20.

Figure 2A:
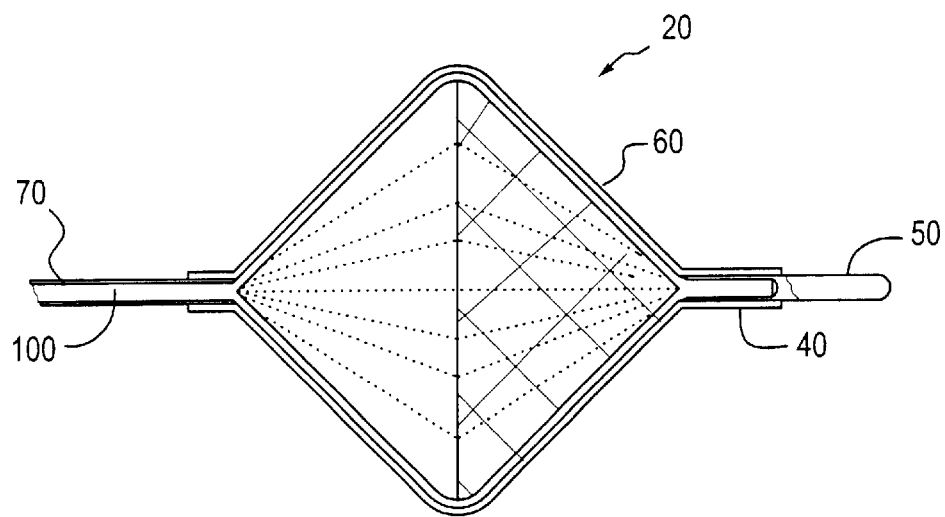
FIGS. 2A and 2B are plan views of a biased closed filter system of a second embodiment of the present invention.
Figure 2B:
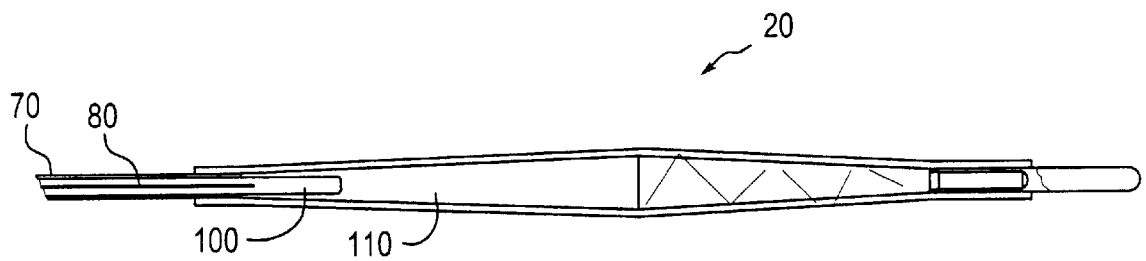

In a second embodiment, as shown in FIGS. 2A and 2B, a biased closed filter assembly 20 is advanced into the vessel of a patient until the treatment site is reached (FIG. 2B). The filter assembly 20 is then deployed into the open position (FIG. 2A) against a vessel wall by advancing an incised actuating wire 100, with a split 80 along its axis, beyond the hollow guidewire 70. The actuating wire 100 expands and pushes the filter assembly 20 into the open position.

Figure 3A:
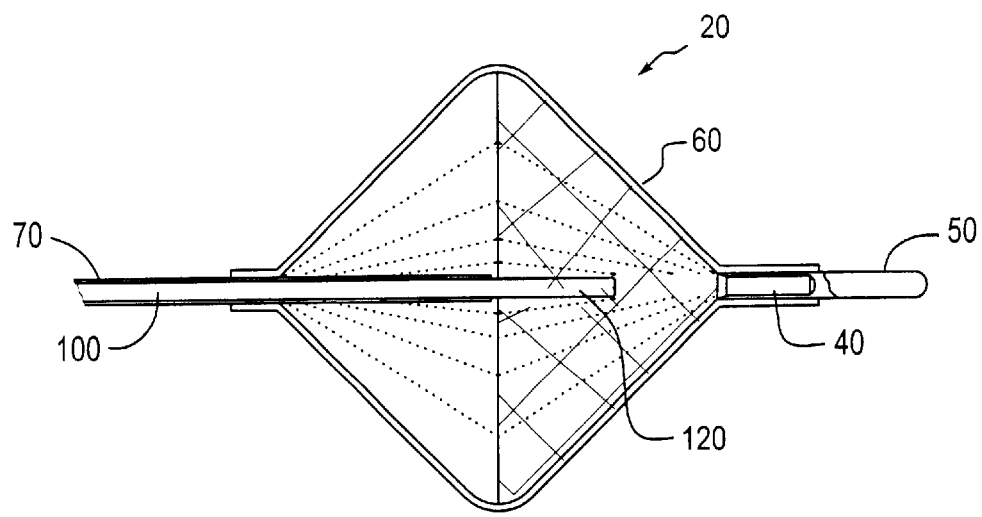
FIGS. 3A and 3B are plan views of a biased open filter system of a third embodiment of the present invention.
Figure 3B:
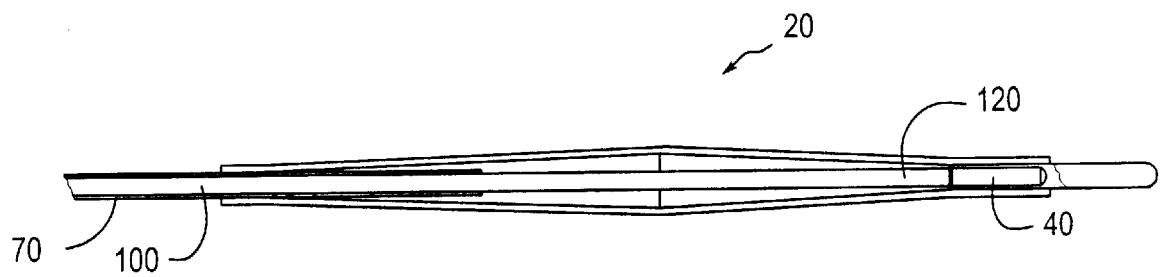

In a third embodiment as shown in FIGS. 3A and 3B, a biased open filter system 20 includes actuating wire 100, having a distal end 120. The distal end 120 is advanced into engagement with the distal end 40 of filter system 20. Further advancement results in the closing of the filter system 20 as shown in FIG. 3B. The filter system 20 is then advanced through the vessel of a patient to the treatment site. The actuating wire 100 is then retracted, resulting in deployment of the filter assembly 20 into the open position in the vessel of the patient (FIG. 3A).

Preferably the distal end 40 of the filter assembly 20 is equipped with a non-traumatic tip 50 attached to or integral with the distal end 40.

Filter Assembly/Membrane

The filter membrane 60 can be made, for example, of various materials, such as a metal, metal alloy, textile or a polymeric material, such as DACRON® or LYCRA® as disclosed in U.S. Pat. No. 5,941,896, Col. 2, lines 43–44.

Figure 5:
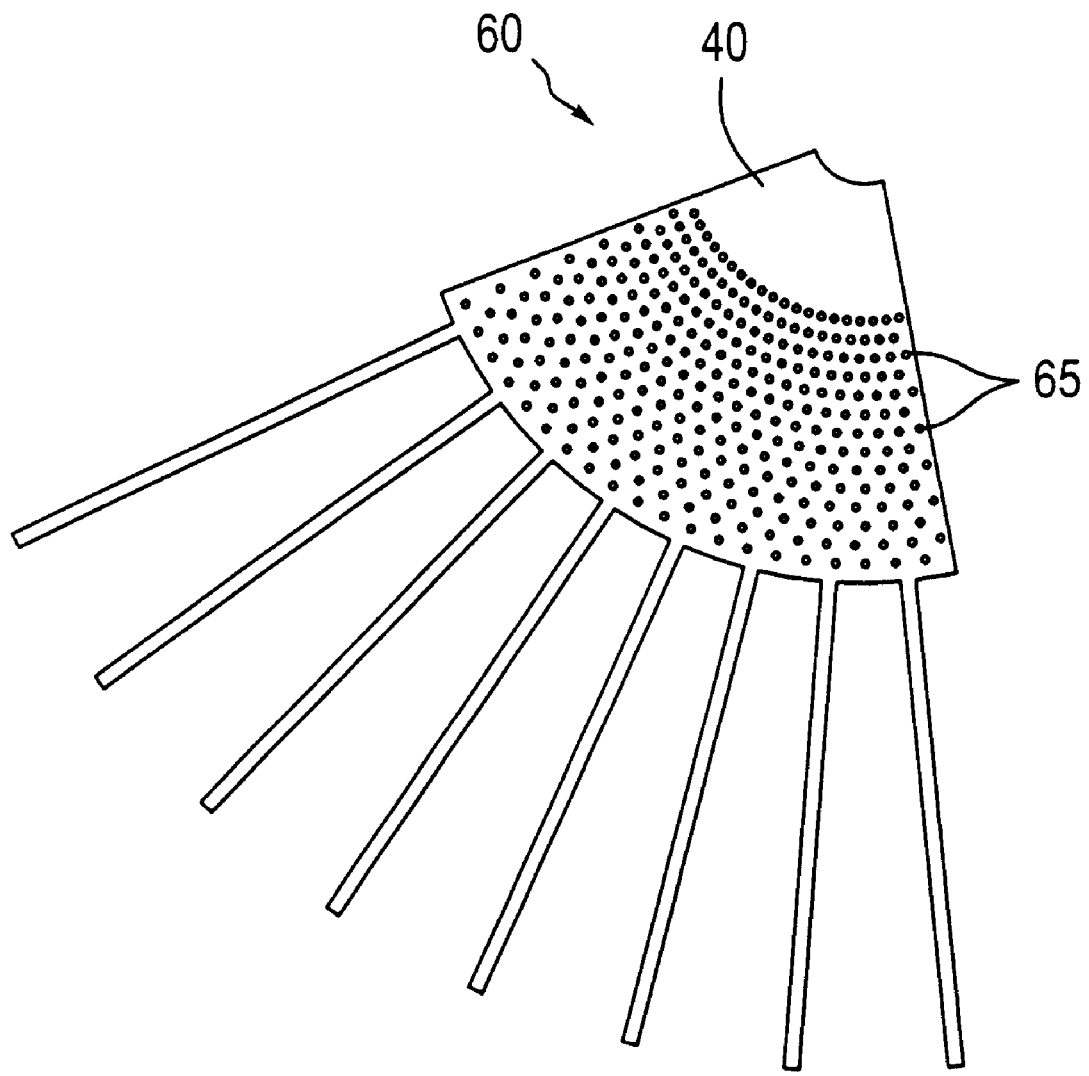
FIG. 5 is a mercator projection of a conical filter membrane with ribs as cut from a single sheet.

The filter membrane can have a mesh structure as shown in FIG. 1, or it may have laser cut openings 65, as shown in FIG. 5. The mesh structure has pores of a sufficient size to block and capture micro- and macro-emboli which may flow downstream from the site where the stenosis is being treated, but large enough such that blood flow is not unduly impeded. The mesh used in the filter device of the invention preferably has a pore diameter under 150 microns, preferably from about 40 to about 100 microns, and more preferably about 80 to 100 microns.

Figure 4A:
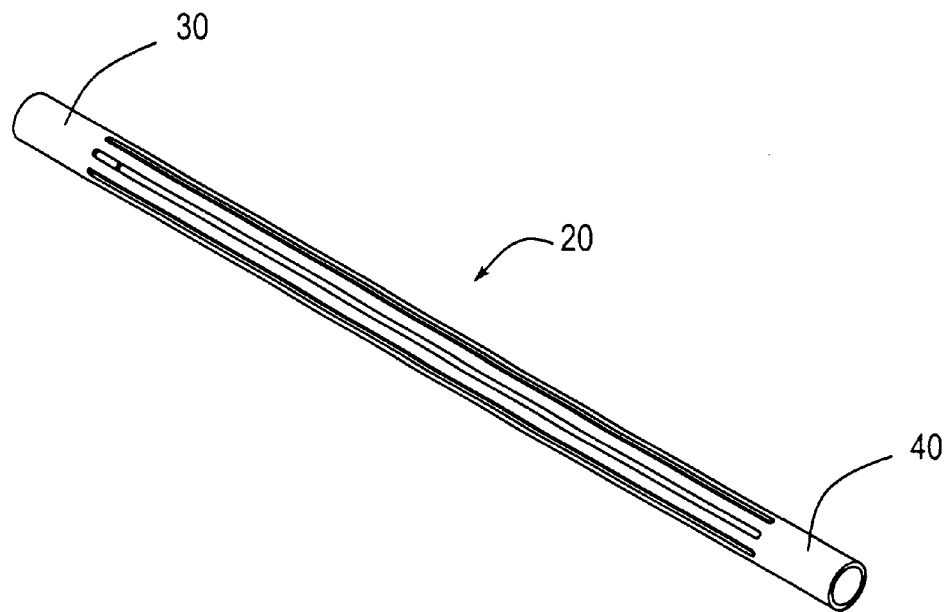
FIGS. 4A and 4B are perspective views of the skeletal structure of a filter assembly.
Figure 4B:
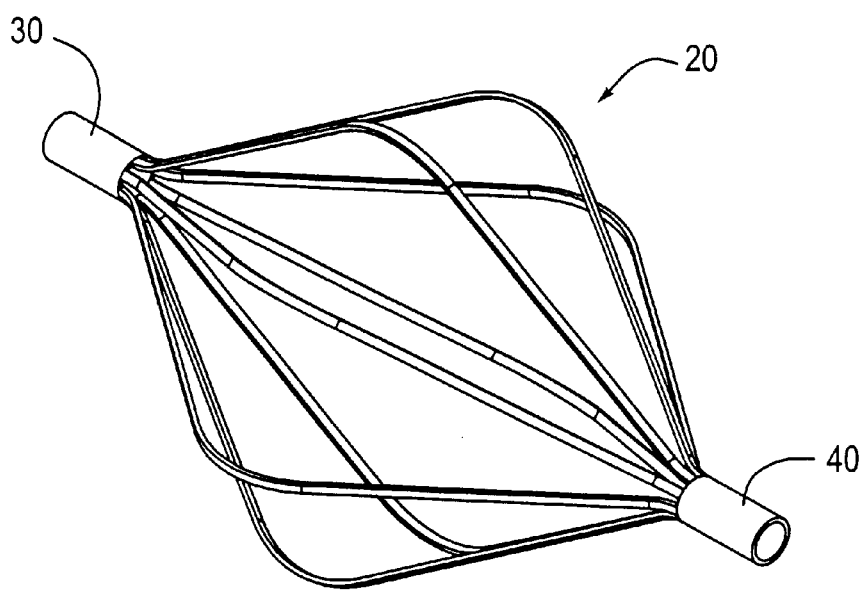

FIG. 4B shows a skeletal structure of a filter assembly 20 while in the deployed position, with ribs expanding radially from the proximal end 30 to the distal end 40, forming a cage. The cage provides support for the filter membrane 60. FIG. 4A shows the filter assembly 20 in the collapsed position.

Preferably, the filter assembly 20, including the filter membrane 60, is made from a single laser cut sheet of a shape memory alloy such as Nitinol® nickel titanium alloy. As disclosed in International Publication WO 96/01591, such alloys tend to have a temperature induced phase change which will cause the material to have a preferred configuration that can be fixed by heating the material above a certain transition temperature to induce a change in the phase of the material. When the alloy is cooled back down, the alloy will "remember" the shape it had during the heat treatment and will tend to assume that configuration unless constrained from so doing. Nitinol®, a preferred shape memory alloy for use in the present invention, is an approximately stoichiometric alloy of nickel and titanium, which may also include other minor amounts of other metals to achieve the desired properties. NiTi alloys such as Nitinol®, including appropriate compositions and handling requirements, are known in the art. See, for example, U.S. Pat. No. 5,067,489 (Lind) and U.S. Pat. No. 4,991,602 (Amplatz et al.), the teachings of which are incorporated by reference.

Figure 6A:
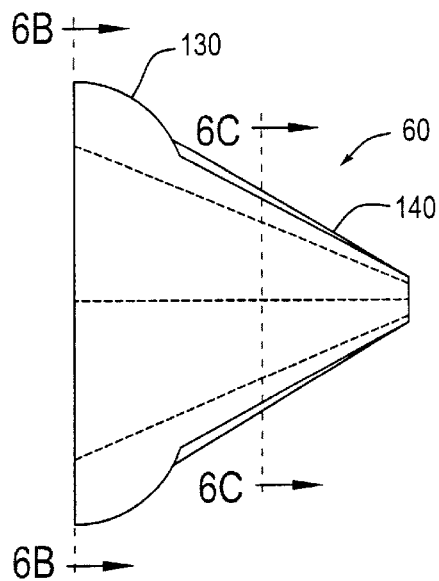
FIGS. 6A, 6B and 6C are views of a filter membrane showing concave and convex folds.
Figure 6B:
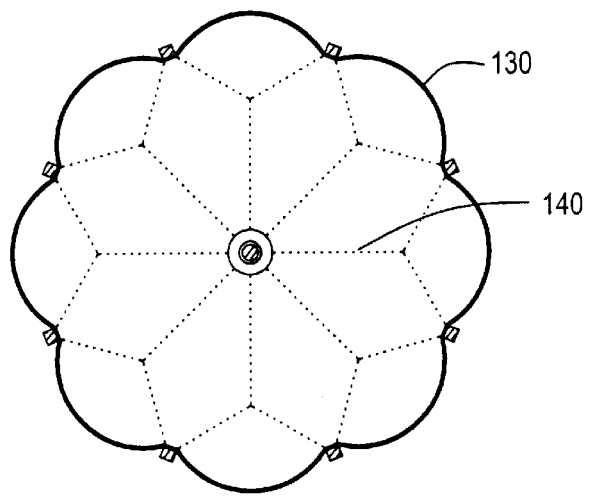
Figure 6C:
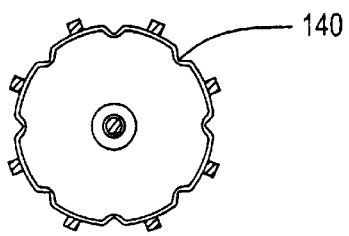

FIGS. 6A–6C show side, front and cross-sectional views, respectively, of an advantageous filter membrane 60 which has convex shapes 130 where it engages the vessel wall and has a distal portion that includes radially extending longitudinal concavities 140 which extend inward further distally as shown in FIG. 6C. The convex shapes 130 cause the filter to form a better seal with the vessel wall and thus force the blood stream into the filter membrane. The concavities 140 assist in the controlled folding of the intravascular filter for positioning or removal.

Figure 7A:
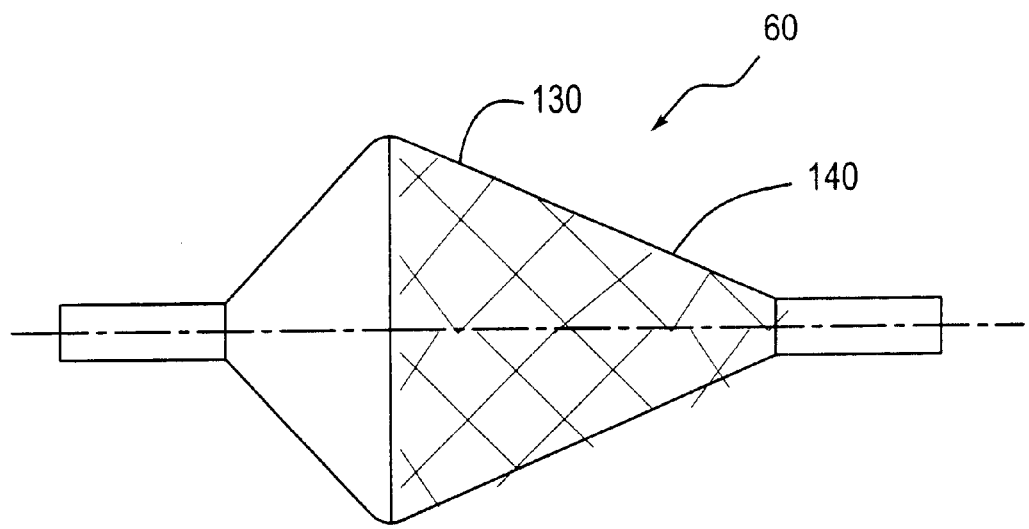
FIGS. 7A and 7B are side views of two embodiments of preferred filter membranes.
Figure 7B:
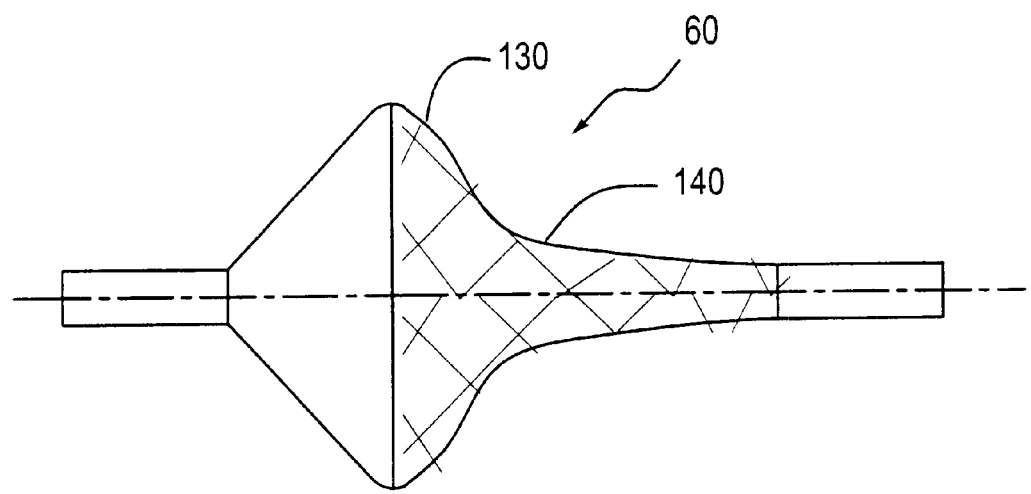

FIG. 7A shows another advantageous filter membrane 60, having a proximal portion 130 and a distal portion 140. The distal portion 140 has an extended frustoconical shape and the proximal portion 130 has a large membrane surface relative to the vessel diameter of a patient. This filter shape forces emboli to be swept further distally into the filter cone by the blood stream, leaving substantial filter surface area to facilitate blood flow. FIG. 7B shows another advantageous filter membrane 60, having a proximal portion 130 and a distal portion 140. The distal portion 140 has a frustoconical or tubular shape when the filter membrane has been deployed. The filter membrane 60 preferably resembles a champagne glass configuration. Once embolic material has engaged the filter membrane 60 it is carried into the distal portion 140 by the blood stream, thus continually cleaning the proximal part 130 of the filter membrane 60 so that it remains fully functional and unclogged.

FIGS. 8A–8D show a device for controlling movement of an actuating wire through a lumen of a hollow guidewire, comprising a first pair of axially constrained grippers 150 configured to grip a proximal portion of the hollow guidewire, a pair of second axially movable grippers 160 configured to grip a portion of the actuating wire extending out of the proximal portion of the hollow guidewire, and a control member 180 such as a knob for moving the axially movable grippers 160 over a predetermined axial distance. Each pair of gripper elements has a space between them for holding the respective guidewire and actuating wire. The device housing 170 preferably comprises a two-piece case, which is hinged at 190 and can be opened to introduce a hollow guidewire 70. The device preferably has at least one clamp 200 for holding the housing closed. The hollow guidewire is held firmly in the constrained grippers 150 and the actuating wire is held by the movable grippers 160 operably connected to a control member 180. The control member 180 can translate rotational movement into the necessary longitudinal movement by means of a cam 181. Upon turning the knob, the cam causes the movable grippers 160 to slide along the hollow guidewire axis, preferably with a 90° turn corresponding to the longitudinal movement desired, for example a 2 mm distance. Optionally, a marker may be placed on the knob to indicate whether the filter position is open or closed.

Figure 9A:
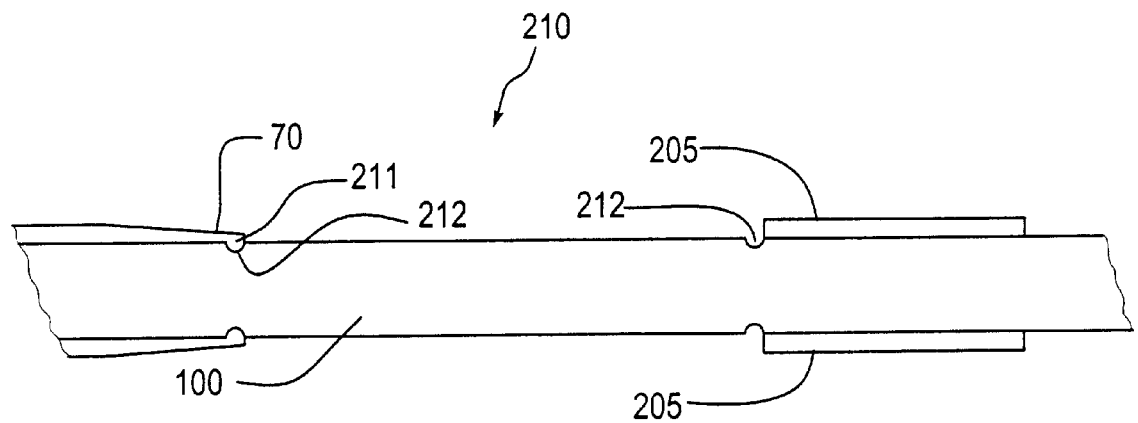
FIG. 9A is a longitudinal cross-sectional view of a first embodiment of a control mechanism with the actuating wire in the fully retracted position.
Figure 9B:
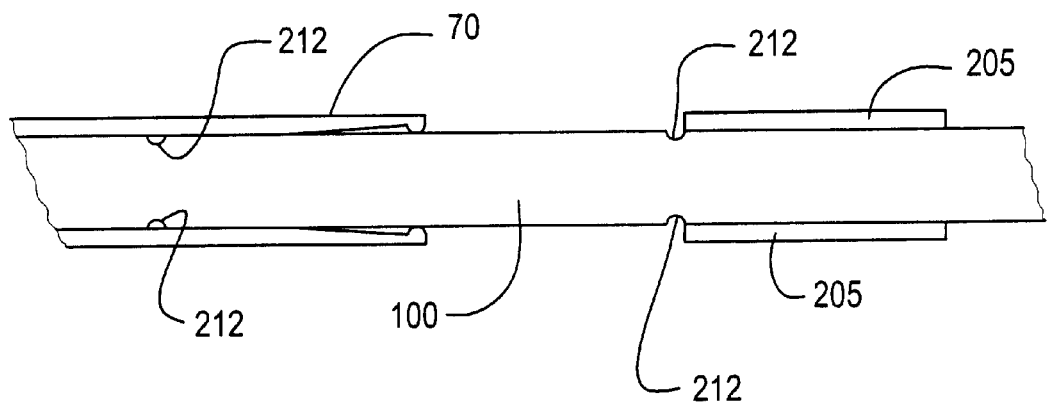
FIG. 9B is a longitudinal cross-sectional view of the embodiment of FIG. 9A with the actuating wire in the partially retracted position.

FIGS. 9 and 10 show two embodiments of a control mechanism 210 for use with an intravascular filter system of the present invention, comprising a hollow guidewire 70 which has an axially extending lumen, an actuating wire 100 extending within the lumen, and a filter assembly that is deployable or collapsible by the actuating wire 100. The control mechanism utilizes projections 211 such as at least one projection on either an interior surface of a hollow guidewire 70 or an exterior surface of an actuating wire 100 and at least one indentation 212 on either of the hollow guidewire 70 or the actuating wire 100. FIGS. 9A and 9B show a first embodiment of the control mechanism 210 with the actuating wire 100 respectively in the fully retracted and partially retracted positions. The mechanism comprises an actuating wire 100 which is equipped with a wire stop 205 and indentations in the form of notches 212 which define actuating wire 100 stop positions. When the actuating wire 100 is fully advanced, the wire stop 205 engages the proximal end of the hollow guidewire 70. The proximal end of the hollow guidewire 70 is shaped so that it engages the notches 212 on the actuating wire 100.

Figure 10A:
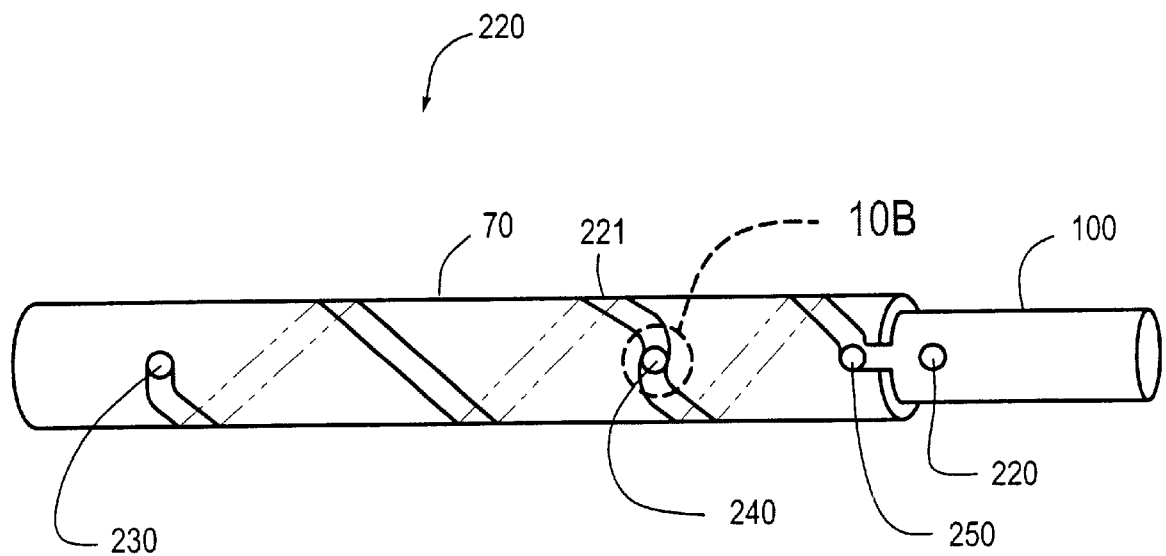
FIGS. 10A and 10B are views of a second embodiment of a control mechanism for an actuating wire.
Figure 10B:
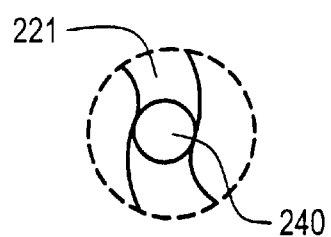

FIGS. 10A and 10B show a second embodiment of a control mechanism 220. The second embodiment features an indentation in the form of a spiral cut 221 at the proximal end of the hollow guidewire 70. A pin 220 mounted on the actuating wire 100 engages the spiral cut 221 upon advancing of the actuating wire 100 into the hollow guidewire 70. The actuating wire 100 thus performs a rotation permitting the operator exact control of the actuating wire 100 movement. As shown in FIG. 10A, three full revolutions of the actuating wire 100 will correspond to the fully advanced position 230. The spiral cut 221 is preferably formed in such a way that the pin 220 can be held in the fully advanced position 230 or in the partially retracted position 240 (shown in an expanded view of FIG. 10B). The mechanism is preferably configured so that the actuating wire 100 may be removed once withdrawn beyond the fully retracted position 250.

Actuating Wire

A preferred class of materials for forming the actuating wire, particularly for the embodiments shown in FIGS. 1 and 2, is shape memory alloys, with Nitinol®, a nickel titanium alloy, being particularly preferred. Suitable heat treatments of Nitinol® wire to set a desired shape are well known in the art. Spirally wound Nitinol® coils, for example, are used in a number of medical applications, such as forming the coils carried around distal lengths of actuating wires. A wide body of knowledge exists for forming Nitinol® wires in such medical devices. It has been found that holding a Nitinol® wire at about 500° C. to about 550° C. for a period of about 1 to about 30 minutes, depending on the softness or hardness of the device to be made, will tend to set the wire in its deformed state, i.e., wherein it conforms to a molding surface of the molding element. At lower temperatures the heat treatment time will tend to be greater (e.g. about one hour at about 350° C.) and at higher temperatures the time will tend to be shorter (e.g. about 30 seconds at about 900° C.). These parameters can be varied as necessary to accomodate variations in the exact composition of the Nitinol®, prior heat treatment of the Nitinol®, the desired properties of the Nitinol® in the finished article, and other factors which will be well known to those of skill in this field.

Deployment of the Filter System

Referring to FIGS. 1 and 2, a hollow guidewire 70 and filter assembly 20 is routed through the patient's vessel. The physician can monitor and help steer the filter assembly through the patient's vessels using radiopaque markers with fluoroscopy as described in International Publication WO 99/44510, hereby incorporated by reference, or other methods known to those of skill in the art. The actuating wire 100 is then advanced beyond the distal portion of the hollow guidewire 70 whereby the distal end of the actuating wire 100 converts into the desired shape and deploys the filter assembly 20 into the open position against the vessel wall. Other devices such as catheter balloons, stents, etc., can then be run over the hollow guidewire 70 and deployed to the treatment site. Upon completion of the procedure, the actuating wire 100 is retracted, and the filter assembly 20 returns to the closed position for removal from the patient's circulation. During insertion and/or removal of the filter assembly, the actuating wire may be present inside the hollow guidewire, may be absent entirely, or may even be replaced with a substitute wire, for example to provide different rigidity properties to the system during insertion and/or removal.

Referring to FIG. 3, an actuating wire 100 may be inserted into the filter assembly 20. The actuating wire 100 is advanced to engage the distal end 40 of the filter assembly 20, and collapse the filter assembly 20 into the closed position. The filter assembly 20 is then routed through the patient's vessel. The physician can monitor the progress of and steer the filter assembly 20 through the patient's arteries as already described. The filter assembly 20 is deployed into the open position upon reaching the treatment site by the physician retracting the actuating wire 100. The actuating wire can remain in the lumen of the guidewire, can be entirely removed from the guidewire, or can be replaced with a substitute wire, for example to affect the rigidity of the guidewire while the filter is deployed. Other devices can then be run over the hollow guidewire 70 and deployed to the treatment site as already described. Upon completion of the procedure, the actuating wire 100 is again advanced into the distal end of the filter assembly 20 to collapse it into the closed position for removal from the patient's circulation. Mechanisms such as those of FIGS. 8–10 can preferably be used to control the extent of movement of the actuating wire during deployment and/or collapse of the filter assembly.

Although the invention has, for the purposes of clarity and understanding, been described in some detail by illustration and example, it will be apparent that changes and modifications may be practiced which still fall within the scope of the invention. Moreover, it will be understood that various features described for any given embodiment or in any reference incorporated herein, can be combined with features of other embodiments described herein.

What is claimed is:

1. A removable filter system for trapping solid materials in a vessel of a patient, comprising:

a filter assembly;

a hollow guidewire having a lumen, a distal end and a proximal end, wherein said distal end of said guidewire is connected to said filter assembly; and an actuating wire movable longitudinally through said lumen of said guidewire and engageable and disengageable with said filter assembly to actuate at least one of deployment and collapse of said filter assembly, wherein said actuating wire is not affixed to said filter assembly.

2. The filter system of claim 1, wherein said filter assembly comprises a biased open filter membrane that can be forced into a closed position by advancing said actuating wire through said lumen and against a distal end of said filter assembly.

3. The filter system of claim 1, wherein said filter assembly comprises a biased closed filter membrane that can be forced into an open position by advancing said actuating wire through said lumen and into said filter assembly, and forming a three-dimensional configuration of a distal end of said actuating wire in said filter assembly.

4. A removable filter system for trapping solid materials in a vessel of a patient, comprising:

a filter assembly comprising a filter membrane, biased in an open position and having a distal end and a proximal end;

a hollow guidewire, having a distal end and a proximal end, wherein said distal end of said hollow guidewire is connected to said proximal end of said filter assembly; and an actuating wire having a proximal end and a distal end, wherein said filter assembly collapses to a closed position as said actuating wire is advanced through said hollow guidewire and into said distal end of said filter assembly, and wherein said filter assembly deploys into the open position as said actuating wire is retracted away from said distal end of said filter assembly.

5. The filter system of claim 4, wherein said filter assembly comprises a plurality of ribs expanding radially from said distal end to said proximal end of said filter assembly and providing a structural support for said filter membrane.

6. The filter system of claim 5, wherein said filter assembly is composed of a shape memory alloy.

7. The filter system of claim 6, wherein said shape memory alloy is a nickel titanium alloy.

8. The filter system of claim 4, wherein said membrane is composed of a polymeric material.

9. The filter system of claim 4, wherein said membrane has a mesh structure.

10. The filter system of claim 4, wherein said membrane has is composed of a polymeric material.

11. The filter system of claim 4, wherein said membrane is composed of a nickel titanium alloy.

12. The filter system of claim 10, wherein said membrane has laser-cut openings.

13. The filter system of claim 11, wherein said membrane has laser-cut openings.

14. The filter system of claim 13, wherein said filter assembly is cut from a single sheet of material.

15. The filter system of claim 4, wherein said filter membrane has a convex fold where said membrane engages said vessel wall and a concave fold distal to said convex fold.

16. The filter system of claim 15, wherein said filter membrane has at least one longitudinal fold.

17. The filter system of claim 4, further comprising a handle; said handle comprising a locking mechanism wherein said actuating wire and said hollow guidewire can be connected at said hollow guidewire proximal end, thereby securing said filter assembly in either the deployed or retracted position.

18. The filter system of claim 17, further comprising a substitute wire that can be inserted in said guidewire upon removal of said actuating wire.

19. A removable filter system for trapping solid materials in a vessel of a patient, comprising:
a filter assembly comprising a filter membrane, biased in a closed position and having a distal end and a proximal end;
a hollow guide wire having a distal end and a proximal end, wherein said distal end of said hollow guidewire is attached to said proximal end of said filter assembly; and
an actuating wire having a proximal end and a distal end, wherein said distal end of said actuating wire is constrained within said hollow guidewire, and wherein said distal end of said actuating wire changes shape to deploy said filter assembly into an open position when said distal end of said actuating wire extends beyond said distal end of said hollow guidewire into said filter assembly; said filter assembly returning to the closed position upon retraction of said actuating wire into said hollow guidewire.

20. The filter system of claim 19, wherein said filter assembly comprises a plurality of ribs expanding radially from said distal end to said proximal end of said filter assembly and providing a structural support for said filter membrane.

21. The filter system of claim 19, wherein at least a portion of said actuating wire is split along its axis, forming an incision, said actuating wire expanding outward to engage and deploy said filter assembly in the open position when said distal end of said actuating wire extends beyond said distal end of said hollow guidewire.

22. The filter system of claim 19, wherein said membrane has a mesh structure.

23. The filter system of claim 19, wherein said membrane is composed of a polymeric material.

24. The filter system of claim 23, wherein said membrane has laser-cut openings.

25. The filter system of claim 19, wherein said membrane is composed of a nickel titanium alloy.

26. The filter system of claim 25, wherein said membrane is cut from a single sheet of material.

27. The filter system of claim 19, wherein said filter membrane has a convex fold where said membrane engages said vessel wall and a concave fold distal to said convex fold.

28. The filter system of claim 27, wherein said filter membrane has at least one longitudinal fold.

29. The filter system of claim 19, wherein said actuating wire is composed of a shape memory alloy.

30. The filter system of claim 29, wherein said shape memory alloy is a nickel titanium alloy.

31. The filter system of claim 19, further comprising a handle; said handle comprising a locking mechanism wherein said actuating wire and said hollow guidewire can be connected at said hollow guidewire's proximal end, thereby securing said filter assembly in either the deployed or retracted position.

32. The filter system of claim 19, wherein said distal end of said actuating wire assumes a spiral shape upon said actuating wire extending beyond said distal end of said hollow guidewire.

33. The filter system of claim 19, wherein said distal end of said actuating wire assumes a lasso shape upon said actuating wire extending beyond said distal end of said hollow guidewire.

34. A method of trapping solid materials in a vessel of a patient, comprising:
inserting a hollow guidewire having a lumen and a distal end connected to a proximal end of a filter assembly into said vessel while said filter assembly is in a closed position, to position said filter assembly in said vessel; and
deploying said filter assembly into an open position in said vessel by longitudinally moving an actuating wire through said lumen of said guidewire, wherein said actuating wire is not affixed to said filter assembly.

35. The method of claim 34, wherein said filter assembly is biased open when at rest, and is forced into said closed position by advancing said actuating wire relative to said lumen and against a distal end of said filter assembly.

36. The method of claim 34, wherein said filter assembly is biased closed when at rest, and is forced into said open position by advancing said actuating wire relative to said lumen and into said filter assembly where a distal end of said actuating wire assumes a three-dimensional configuration that forces said filter assembly into said open position.

37. An intravascular filter, comprising:
a cage comprising a plurality of ribs extending from a proximal end of said cage to a distal end of said cage, said ribs being constrained against radial movement to a vessel wall at said distal end of said cage and being radially movable into contact with said vessel wall at said proximal end of said cage; and
a filter membrane supported within said cage, said filter membrane including a proximal portion that includes radial convexities extending radially outward between said ribs to contact said vessel wall when said intravascular filter is in a deployed condition.

38. An intravascular filter according to claim 37, said filter membrane including a distal portion that includes radial concavities extending radially inward between said ribs to assist in controlled folding of said intravascular filter for positioning or removal.

39. An intravascular filter according to claim 38, wherein said proximal portion of said filter membrane is axially convex and said distal portion of said filter membrane is frustoconical when said intravascular filter is in said deployed condition.

40. An intravascular filter according to claim 38, said filter membrane including a transition area where said radial convexities transition into said radial concavities.

41. An intravascular filter according to claim 40, wherein said transition area is at a meeting point of said proximal portion and said distal portion.

42. An intravascular filter comprising a filter membrane, said filter membrane, when in a deployed condition, including a proximal portion that is axially convex, and a distal portion that is frustoconical or tubular and of a smaller diameter than said proximal portion.

43. An intravascular filter system, comprising:

a hollow guidewire having an axially extending lumen;

an actuating wire extending within said lumen; and a filter assembly that can be deployed and/or collapsed by said actuating wire; and a control mechanism for controlling an extent of axial movement of said actuating wire through said lumen; wherein said control mechanism comprises:

at least one projection on at least one of an interior surface of said guidewire and an exterior surface of said actuating wire, and at least one mating indentation on the other of said guidewire and said actuating wire.

44. An intravascular filter system according to claim 43, wherein said at least one indentation comprises a groove with a distal terminus that prevents further axial movement of said projection in a distal direction.

45. An intravascular filter system according to claim 44, wherein said spiral groove is on an interior surface of said guidewire and said projection is on an exterior surface of said actuating wire, and a proximal end of said groove is located at a proximal edge of said guidewire to permit withdrawal of said actuating wire from said guidewire.

46. An intravascular filter system according to claim 44, wherein said groove includes at least one feature that identifies a preferred distance of axial movement of said actuating wire in a proximal direction.

47. An intravascular filter system according to claim 46, wherein said groove has a spiral shape.

48. An intravascular filter system according to claim 46, wherein said preferred distance is a distance required to deploy and/or collapse said filter.

49. An intravascular filter system according to claim 43, wherein at least one said indentation or projection is located at a proximal end portion of said guidewire, and a first said mating projection or indentation is located at a position on said actuating wire corresponding to an advanced position of said actuating wire relative to said filter assembly.

50. An intravascular filter system according to claim 49, wherein a second said mating projection or indentation is located at a position on said actuating wire corresponding to a position of said actuating wire wherein said actuating wire is retracted relative to said filter assembly.

51. An intravascular filter system according to claim 50, further comprising a stop that prohibits distal movement of said actuating wire beyond a fully advanced position relative to said filter assembly, but said actuating wire is not completely constrained from being fully retracted from said guide wire.

52. A device for controlling movement of an actuating wire through a lumen of a hollow guidewire, comprising:

a first, axially constrained gripper configured to grip a proximal portion of said hollow guidewire;

a second, axially movable gripper configured to grip a portion of said actuating wire extending out of said proximal portion of said hollow guidewire; and a control member for moving said axially movable gripper over a predetermined axial distance.

53. A device for controlling movement of an actuating wire through a lumen of a hollow guidewire, comprising:

a first, axially constrained gripper configured to grip a proximal portion of said hollow guidewire;

a second, axially movable gripper configured to grip a portion of said actuating wire extending out of said proximal portion of said hollow guidewire; and a control member for moving said axially movable gripper over a predetermined axial distance;

wherein each said gripper comprises a pair of gripper elements with a space between them for holding the respective guidewire or actuating wire.

54. A device according to claim 53, wherein said control member comprises a rotatable knob operably connected to said second gripper.

55. A device according to claim 53, further comprising a housing configured to clamp said pairs of gripper elements onto said respective guidewire and actuating wire when said housing is closed.

56. A device according to claim 55, wherein said housing includes at least one clamp for holding said housing closed.

57. A device according to claim 56, wherein said housing further includes at least one hinge for allowing said housing to open and be placed onto said guidewire and said actuating wire from the side of said wires.

58. A filter assembly comprising:

a filter membrane;

a distal end and a proximal end; said assembly having ribs expanding radially from said distal end to said proximal end defining a filter cage and providing structural support for said filter membrane, wherein said filter cage and said filter membrane are formed from a single sheet of a shape memory alloy.

59. The filter assembly of claim 58, wherein said membrane has laser cut openings.

60. A filter assembly comprising:

a filter membrane;

a distal end and a proximal end; said assembly having ribs expanding radially from said distal end to said proximal end defining a filter cage and providing structural support for said filter membrane, wherein said filter cage and said filter membrane are formed from a single sheet of a polymeric material.

61. A filter assembly comprising:

a filter membrane;

a distal end and a proximal end; said assembly having ribs expanding radially from said distal end to said proximal end defining a filter cage and providing structural support for said filter membrane, wherein said filter cage and said filter membrane are formed from a single sheet of a polymeric material;

wherein said filter membrane has laser cut openings.

* * * * *